(12) United States Patent
Isaacson et al.

(10) Patent No.: US 10,328,251 B2
(45) Date of Patent: Jun. 25, 2019

(54) SYSTEMS AND METHODS TO PREVENT CATHETER OCCLUSION

(71) Applicant: Becton, Dickinson and Company, Franklin Lakes, NJ (US)

(72) Inventors: S Ray Isaacson, Layton, UT (US); Erik K Witt, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 143 days.

(21) Appl. No.: 15/477,587

(22) Filed: Apr. 3, 2017

(65) Prior Publication Data

US 2018/0280680 A1 Oct. 4, 2018

(51) Int. Cl.
*A61M 25/00* (2006.01)
*A61M 39/16* (2006.01)
(Continued)

(52) U.S. Cl.
CPC ............ *A61M 39/16* (2013.01); *A61B 5/05* (2013.01); *A61B 8/12* (2013.01); *A61B 90/70* (2016.02); *A61L 2/025* (2013.01); *A61M 5/16831* (2013.01); *A61M 25/00* (2013.01); *A61M 25/0017* (2013.01); *A61M 25/0068* (2013.01); *A61N 7/00* (2013.01); *B08B 17/02* (2013.01); *G16H 20/17* (2018.01); *G16H 40/63* (2018.01); *A61B 2090/701* (2016.02); *A61M 2025/0019* (2013.01); *A61M 2039/167* (2013.01); *A61M 2205/0294* (2013.01); *A61M 2205/058* (2013.01); *A61M 2205/3375* (2013.01);
(Continued)

(58) Field of Classification Search
CPC .... A61B 5/05; A61B 8/12; A61M 2205/0294; A61M 2205/058; A61M 2205/3375; A61M 2205/50; A61M 25/0017; A61M 5/16831; A61N 2007/0052; A61N 7/00
See application file for complete search history.

(56) References Cited

U.S. PATENT DOCUMENTS

| 5,188,620 A | 2/1993 | Jepson et al. |
| 2005/0038376 A1* | 2/2005 | Zumeris .................. A61L 2/02 604/22 |

(Continued)

FOREIGN PATENT DOCUMENTS

| EP | 243458 | 2/1994 |
| EP | 1511414 | 8/2012 |

*Primary Examiner* — Rebecca E Eisenberg
(74) *Attorney, Agent, or Firm* — Kirton & McConkie; Craig Metcalf; Kevin Stinger

(57) ABSTRACT

A system to detect occlusion of an intravenous catheter may include a housing, which may include a distal end configured to couple to a proximal end of a catheter adapter and an inner lumen forming a fluid pathway. The system may also include one or more transmitters, which may be disposed within the housing. The transmitters may be configured to transmit first energy waves along a length of an intravenous catheter at a first frequency, and a portion of the first energy waves that are reflected back from the catheter may be detected by the system. Based on the portion of the first energy waves that are reflected back from the catheter, the transmitters may transmit second energy waves along the length of the catheter at a second frequency, which may be greater than the first frequency and configured to reduce formation of blood clots within the catheter.

16 Claims, 8 Drawing Sheets

(51) Int. Cl.

| | | |
|---|---|---|
| *A61M 5/168* | (2006.01) | |
| *A61N 7/00* | (2006.01) | |
| *A61B 90/70* | (2016.01) | |
| *A61B 8/12* | (2006.01) | |
| *A61B 5/05* | (2006.01) | |
| *A61L 2/025* | (2006.01) | |
| *B08B 17/02* | (2006.01) | |
| *G16H 40/63* | (2018.01) | |
| *G16H 20/17* | (2018.01) | |
| *B08B 7/02* | (2006.01) | |

(52) U.S. Cl.
CPC .. *A61M 2205/50* (2013.01); *A61N 2007/0052* (2013.01); *B08B 7/028* (2013.01)

(56) References Cited

U.S. PATENT DOCUMENTS

| | | |
|---|---|---|
| 2009/0188531 A1 | 7/2009 | Boyle, Jr. et al. |
| 2011/0160643 A1 | 6/2011 | Dacey et al. |
| 2017/0340801 A1* | 11/2017 | Roger ................. A61M 1/3656 |

\* cited by examiner

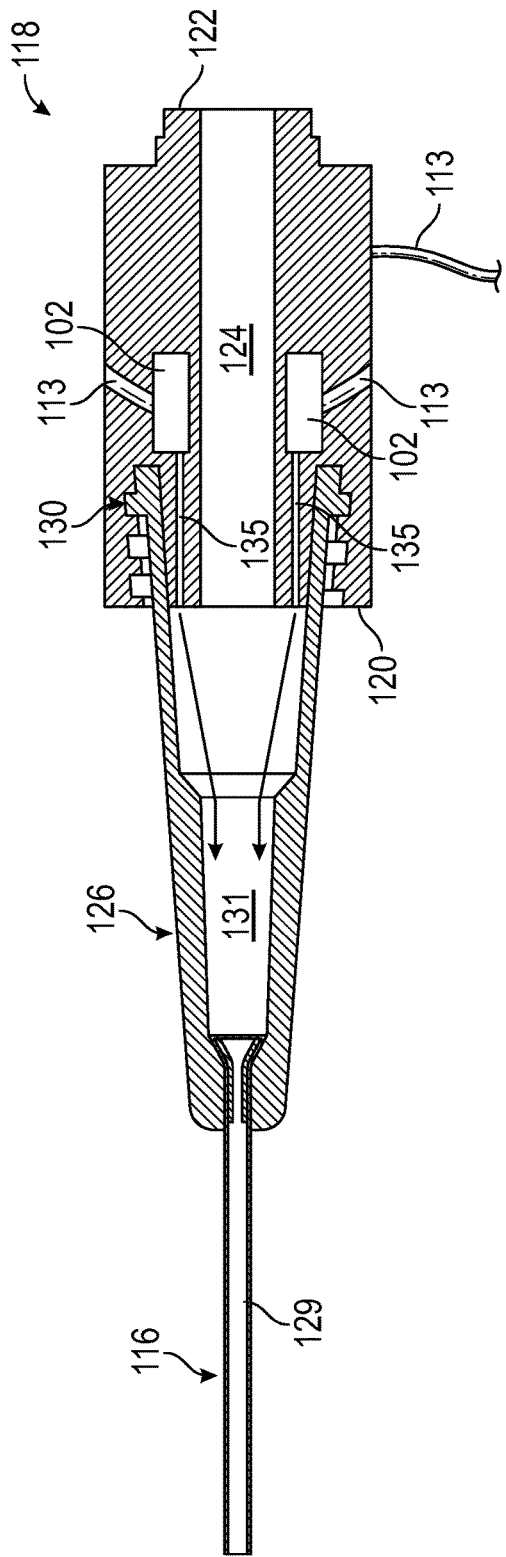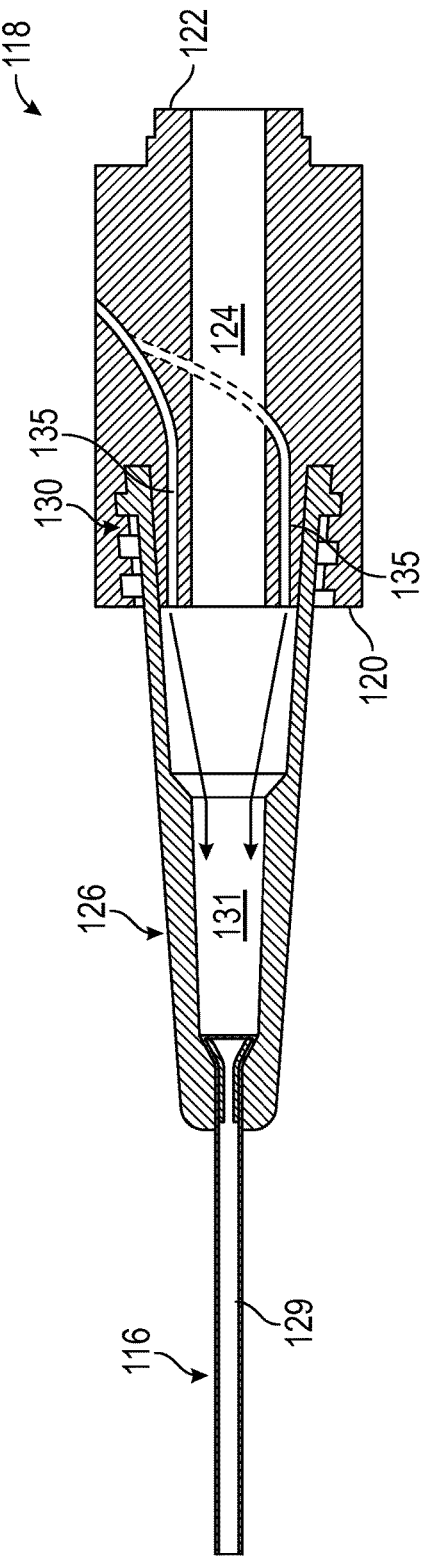

SYSTEMS AND METHODS TO PREVENT CATHETER OCCLUSION

BACKGROUND OF THE INVENTION

In some instances, an intravenous (IV) catheter, including a peripheral IV catheter, may become unusable or compromised prior to completion of infusion or blood withdrawal using the catheter. One reason the catheter may become unusable may be due to occlusion of the catheter over time. Occlusion may result from non-use of the catheter and/or diffusion of blood from the vein slowly into a distal tip of the catheter. In response to the catheter becoming occluded, the catheter may need to be removed and replaced with a new catheter. Catheter occlusions may be thrombotic, resulting from formation of a blood clot or thrombus within or surrounding the distal tip of the catheter. Catheter occlusions may also be non-thrombotic, resulting from precipitates, mechanical obstructions, and other factors. Further, catheter occlusions can lead to catheter infection, pulmonary embolism, post-thrombotic syndrome, and other negative health outcomes.

Accordingly, there is a need in the art for devices, systems, and methods that prevent catheter occlusion. Such devices, systems, and methods are disclosed in the present disclosure.

BRIEF SUMMARY OF THE INVENTION

The present disclosure relates generally to prevention of IV catheter occlusion. In particular, the present disclosure relates to devices, systems, and associated methods to prevent IV catheter occlusion. In some embodiments, a system to prevent occlusion of an intravenous catheter may include a housing, which may include a distal end, a proximal end, and an inner lumen forming a fluid pathway. In some embodiments, the inner lumen may extend between the distal end and the proximal end of the housing.

In some embodiments, the system may include a catheter adapter. In some embodiments, the catheter may extend distally from a distal end of the catheter adapter. In some embodiments, the fluid pathway may extend through an inner lumen of the catheter and the catheter adapter. In some embodiments, the distal end of the housing may be configured to couple to a proximal end of the catheter adapter. In some embodiments, the housing may be integrally formed with the catheter adapter and/or may include or correspond to a portion of the catheter adapter.

In some embodiments, the housing may include one or more transmitters, which may transmit energy waves along a length of the catheter and/or the catheter adapter. In some embodiments, the transmitters may transmit first energy waves along a length of the catheter of the catheter adapter at a first frequency and/or second energy waves along the length of the catheter of the catheter adapter at a second frequency. In some embodiments, separate transmitters may transmit the first energy waves along the length of the catheter and the second energy waves along the length of the catheter. In some embodiments, the transmitters may include sonic or ultrasound wave transmitters that transmit ultrasonic or sonic waves. In some embodiments, the transmitters may include electromagnetic wave transmitters that transmit electromagnetic waves, including, radio waves, infrared, visible light, ultraviolet, X-rays, or gamma rays.

In some embodiments, the housing may include one or more transducers, which may detect a portion of the energy waves that are reflected back from the catheter. In some embodiments, the transducers and/or the transmitters may be disposed in the fluid pathway, disposed partially within the fluid pathway, or separated from the fluid pathway by a buffer element, such as, for example, a membrane, coating, adhesive, or another suitable element. In some embodiments, the transmitters may be disposed in any location within the housing that allows them to transmit the energy waves along the length of the catheter. In some embodiments, the transducers may be disposed in any location within the housing that allows them to receive the portion of the energy waves that are reflected back from the catheter. In some embodiments, the transducers and/or transmitters may be embedded or encapsulated in a wall of the inner lumen of the housing.

In some embodiments, the transducers may detect a portion of the first energy waves that are reflected back from the catheter and/or convert the portion of the first energy waves that are reflected back from the catheter to an electrical signal.

In some embodiments, the transducers may each include one or more piezoelectric elements, such as, for example, piezoelectric crystals. In some embodiments, the piezoelectric elements may act as the transmitters. In some embodiments, a particular piezoelectric element may transmit the first energy waves along the length of the catheter. In some embodiments, a same or different piezoelectric element may receive the portion of the first energy waves that are reflected back from the catheter and convert the portion to a corresponding electrical signal. Additionally or alternatively, in some embodiments, a particular piezoelectric element may transmit the second energy waves along the length of the catheter at the second frequency.

In some embodiments, the second frequency may be configured to ablate and/or dislodge any clotting material before it forms a blood clot within the catheter. For example, the transmitters may transmit second energy waves, which may include microwaves having frequencies between approximately 300 MHz and approximately 300 GHz. As another example, the piezoelectric elements may be constructed of a material and/or shaped such that particular piezoelectric elements resonate at the second frequency between approximately 300 kHz and approximately 700 kHz or between approximately 500 and approximately 700 kHz or another frequency that reduces a mass of forming vascular occlusions.

In some embodiments, the second frequency may be greater than the first frequency. For example, the first frequency may be less than or equal to 300 MHz. As another example, other particular piezoelectric elements may be constructed of a material and/or shaped such that the other piezoelectric elements resonate at the first frequency of less than approximately 300 kHz or less than approximately 500 kHz. In some embodiments, the first frequency may be suitable for sensing or detection of blood clots occluding the catheter occlusion and/or clotting material that may lead to occlusion of the catheter, and the second frequency may be suitable for removal of the clotting material and/or the blood clot from within the catheter. In some embodiments, the second energy waves may be transmitted along the length of the catheter after the first energy waves are transmitted along the length of the catheter.

In some embodiments, the transmitters may not transmit the first energy waves at the first frequency for purposes of detecting a blood clot or clotting material that may form a clot. In these and other embodiments, the system may not include or utilize any sensing elements. In some embodiments, the system may not include and/or utilize any transducers and may not detect the portion of the energy waves that are reflected back from the catheter. In some embodiments, the second energy waves may be transmitted regularly, such as once a day, once an hour, once per shift of a healthcare worker, etc. The regular transmission of the second energy waves at the second frequency may prevent blood from clotting and/or sticking to the distal tip of the catheter.

In some embodiments, the system may include a processor, which may be coupled to the transducers and/or the transmitters. In some embodiments, the processor may receive the electrical signal corresponding to the portion of the first energy waves that are reflected back from the catheter. In some embodiments, the processor may compare the electrical signal to a baseline electrical signal to determine a difference between the electrical signal and the baseline electrical signal.

In some embodiments, the transmitters may transmit the second energy waves along the intravenous catheter at the second frequency in response to the difference between the electrical signal and the baseline electrical signal being below a threshold value. In some embodiments, the threshold value may correspond to a particular difference between the electrical signal and the baseline electrical signal that indicates that a blood clot is likely fully formed and it would not be desirable to sonically vibrate the blood clot loose into a blood stream of a patient.

In some embodiments, the transmitters may continuously transmit the second energy waves along the length of the intravenous catheter at the second frequency, which may continuously vibrate a distal tip of the catheter and prevent blood from clotting or sticking to the distal tip of the catheter. For example, the second energy waves may be continuously transmitted from approximately a time when the catheter is inserted into a vein of a patient until a time when the catheter is removed from the vein and/or until infusion and/or blood withdrawal using the catheter is complete. As another example, the second energy waves may be continuously transmitted for a period of minutes to hours.

In some embodiments, the transmitters may transmit the second energy waves along the length of the catheter at the second frequency in one or more pulses. In some embodiments, each of the pulses may vibrate the distal tip of the catheter and prevent blood from clotting or sticking to the distal tip of the catheter. In some embodiments, a timing of the pulses may be evenly spaced apart. In some embodiments, time between pulses may be less than a second, every few seconds, or another period of time. In some embodiments, the transmitters may cease or be prevented from transmitting the second energy waves along the length of the catheter at the second frequency in response to the difference between the electrical signal and the baseline signal meeting the threshold value. For example, the transmitters may cease continuously transmitting the second energy waves along the length of the catheter at the second frequency and/or transmitting the second energy waves along the length of the catheter at the second frequency in one or more pulses.

In some embodiments, the baseline electrical signal may be determined by transmitting, via the transmitters, third energy waves, which may include sonic, ultrasonic, and/or electromagnetic waves, along the length of the catheter when the catheter is open or unoccluded and converting a portion of the third ultrasonic waves that are reflected back from the catheter to the baseline electrical signal. In some embodiments, the baseline electrical signal may be determined prior to transmitting the first energy waves along the length of the intravenous catheter and/or converting the portion of the first energy waves that are reflected back from the intravenous catheter to the corresponding electrical signal. For example, the baseline electrical signal may be determined immediately after or shortly after insertion of the catheter into the vein of the patient.

In some embodiments, an outer surface of a distal tip of the intravenous catheter may include one or more facets and/or curved portions, which may improve reflection of the first and/or second energy waves. In some embodiments, a wall forming the inner lumen of the catheter may include one or more facets and/or curved portions, which may improve reflection of the first and/or second energy waves.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIG. 2D illustrates another cross-sectional view of the portion of the system, according to some embodiments;

FIG. 2E illustrates another cross-sectional view of the portion of the system, according to some embodiments;

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments, represented in FIGS. 1 through 5, is not intended to limit the scope of the invention, as claimed, but is merely representative of some embodiments of the invention.

Figure 1:
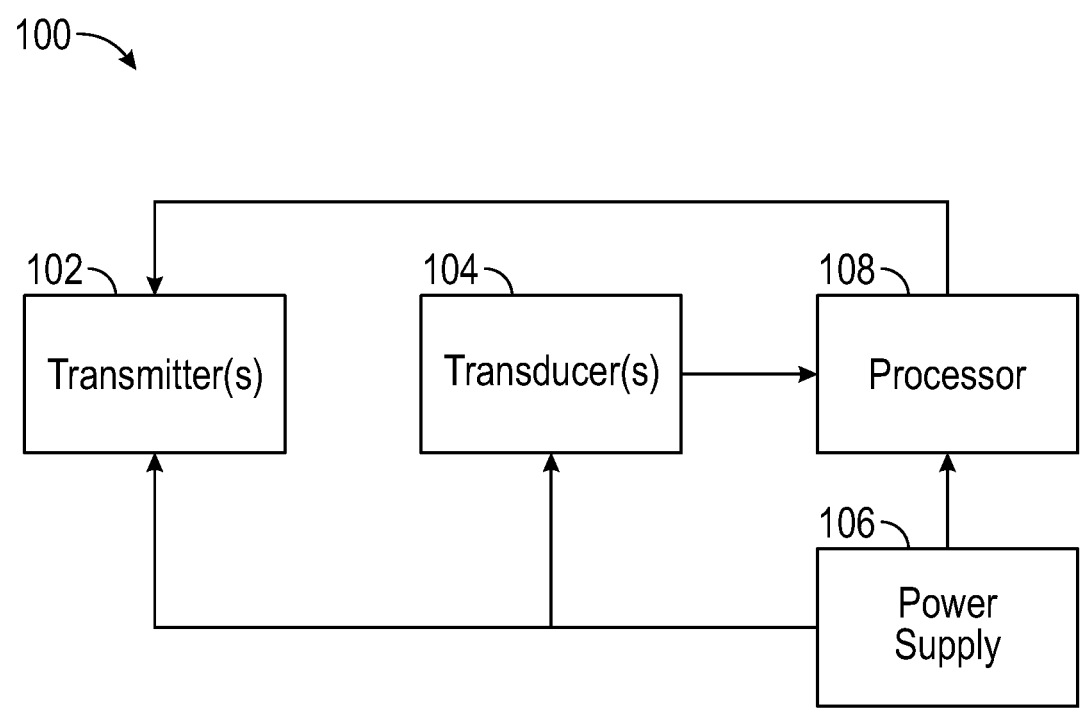
FIG. 1 illustrates a block diagram of an example system to detect catheter occlusion, according to some embodiments.

Generally, the present disclosure relates generally to prevention of IV catheter occlusion. In particular, the present disclosure relates to devices, systems, and associated methods to prevent IV catheter occlusion. Referring now to FIG. 1, in some embodiments, a self-diagnosing catheter assembly or system 100 may include one or more transmitters 102, which may transmit first energy waves along a length of an intravenous catheter of the catheter adapter at a first frequency and/or second energy waves along the length of the catheter of the catheter adapter at a second frequency. In some embodiments, separate transmitters 102 may transmit the first energy waves along the length of the catheter and the second energy waves along the length of the catheter. In some embodiments, the transmitters 102 may include ultrasound wave transmitters that transmit ultrasonic waves or sonic wave transmitters that transmit sonic waves. In some embodiments, the transmitters 102 may include electromagnetic wave transmitters that transmit electromagnetic waves, including, radio waves, microwaves, infrared, visible light, ultraviolet, X-rays, or gamma rays.

In some embodiments, the system 100 may include one or more transducers 104, which may detect a portion of the energy waves that are reflected back from the catheter. In some embodiments, the transducers 104 and/or the transmitters 102 may be disposed in the fluid pathway, disposed partially within the fluid pathway, or separated from the fluid pathway by a buffer element 139, such as, for example, a membrane, coating, adhesive, or another suitable element. In some embodiments, the transmitters 102 may be disposed in any location within the housing that allows them to transmit the energy waves along the length of the catheter. In some embodiments, the transducers 104 may be disposed in any location within the housing that allows them to receive the portion of the energy waves that are reflected back from the catheter. In some embodiments, the transmitters 102 and/or transducers 104 may be embedded or encapsulated in a wall of the inner lumen of the housing. In some embodiments, the transducers 104 may detect a portion of the first energy waves that are reflected back from the catheter and/or convert the portion of the first energy waves that are reflected back from the catheter to an electrical signal.

In some embodiments, the transducers 104 may each include one or more piezoelectric elements, such as, for example, piezoelectric crystals. In some embodiments, the transmitters 102 may include or correspond to the piezoelectric elements. In some embodiments, a particular piezoelectric element may transmit the first energy waves along the length of the catheter. In some embodiments, a same or different piezoelectric element may receive the portion of the first energy waves that are reflected back from the catheter and convert the portion to a corresponding electrical signal. Additionally or alternatively, in some embodiments, a particular piezoelectric element may transmit the second energy waves along the length of the catheter at the second frequency.

In some embodiments, the second frequency may be configured to ablate and/or dislodge any clotting material before it forms a blood clot within the catheter. For example, the transmitters may transmit second energy waves, which may include microwaves having frequencies between approximately 300 MHz and approximately 300 GHz. As another example, the piezoelectric elements may be constructed of a material and/or shaped such that particular piezoelectric elements resonate at the second frequency of between 300-700 kHz or between 500-700 kHz or another frequency that reduces a mass of forming vascular occlusions.

In some embodiments, the second frequency may be greater than the first frequency. For example, the first frequency may be below 300 MHz. For example, other particular piezoelectric elements may be constructed of a material and/or shaped such that the other piezoelectric elements resonate at the first frequency of less than 300-700 kHz or less than 500-700 kHz. In some embodiments, the first frequency may be suitable for sensing or detection of blood clots occluding the catheter occlusion and/or clotting material that may lead to occlusion of the catheter, and the second frequency may be suitable for removal of the clotting material and/or the blood clot from within the catheter. In some embodiments, the second energy waves may be transmitted along the length of the catheter after the first energy waves are transmitted along the length of the catheter.

In some embodiments, the transmitters 102 may not transmit the first energy waves at the first frequency for purposes of detecting a blood clot or clotting material that may form a clot. In these and other embodiments, the system 100 may not include or utilize any sensing elements. In some embodiments, the system 100 may not include and/or utilize any transducers 104 and may not detect the portion of the energy waves that are reflected back from the catheter. In some embodiments, the second energy waves may be transmitted regularly, such as once a day, once an hour, once per shift of a healthcare worker, etc. In some embodiments, the regular transmission of the second energy waves at the second frequency may prevent blood from clotting and/or sticking to the distal tip of the catheter.

In some embodiments, the transmitters 102 may be coupled with a power supply 106. Additionally, in some embodiments, the system 100 may include a signal generator, which may be coupled to the power supply 106. In some embodiments, the signal generator may be coupled with the transmitters 102. In some embodiments, the signal generator may excite the one or more first transmitters 102, which may result in propagation of the first energy waves throughout the inner lumen of the catheter and/or one or more other portions of the fluid pathway. Additionally or alternatively, in some embodiments, the signal generator may excite one or more second transmitters 102, which may result in propagation of the second energy waves throughout the inner lumen of the catheter and/or one or more other portions of the fluid pathway. The propagation of the first energy waves at the first frequency may provide vibration of fluid within the fluid pathway, which may be easily altered by presence of one or more blood clots within the catheter.

In some embodiments, the system 100 may include a processor 108, which may be coupled to the transducers 104. In some embodiments, the processor 108 may receive the electrical signal corresponding to the portion of the energy waves that are reflected back from the catheter. For example, the processor 108 may receive the electrical signal corresponding to the portion of the first energy waves that are reflected back from the catheter. In some embodiments, the processor 108 may compare the electrical signal to a baseline electrical signal to determine a difference between the electrical signal and the baseline electrical signal. In some embodiments, the difference may indicate whether it is safe to transmit the second energy waves at the second frequency or if potential dislodgement of the blood clot should be avoided.

In some embodiments, the transmitters 102 may transmit the second energy waves along the catheter at the second frequency in response to the difference between the electrical signal and the baseline electrical signal being below a threshold value. In some embodiments, the transmitters 102 may receive input from the processor that indicates whether the difference between the electrical signal and the baseline electrical signal is below, at, or above the threshold value. In some embodiments, the threshold value may correspond to a particular difference between the electrical signal and the baseline electrical signal that indicates that a blood clot is likely fully formed within the catheter, and it would not be desirable to sonically vibrate the clot loose into a blood stream of a patient.

In some embodiments, the transmitters 102 may continuously transmit the second energy waves along the length of the intravenous catheter at the second frequency, which may continuously vibrate a distal tip of the catheter and prevent blood from clotting or sticking to the distal tip of the catheter. For example, the second energy waves may be continuously transmitted from approximately a time when the catheter is inserted into a vein of a patient until a time when the catheter is removed from the vein and/or until infusion and/or blood withdrawal using the catheter is complete. As another example, the second energy waves may be continuously transmitted for a period of minutes to hours. In some embodiments, the transmitters 102 may transmit the second energy waves at regular intervals, such as, for example, once every half hour, once an hour, once a day, etc.

In some embodiments, the transmitters 102 may transmit the second energy waves along the length of the catheter at the second frequency in one or more pulses. In some embodiments, each of the pulses may vibrate the distal tip of the catheter and prevent blood from clotting or sticking to the distal tip of the catheter. In some embodiments, a timing of the pulses may be evenly spaced apart. In some embodiments, the transmitters 102 may cease or be prevented from transmitting the second energy waves along the length of the catheter at the second frequency in response to the difference between the electrical signal and the baseline signal meeting the threshold value. For example, in response to the difference between the electrical signal and the baseline signal meeting the threshold value, for safety of the patient, the transmitters 102 may cease continuously transmitting the second energy waves along the length of the catheter at the second frequency and/or transmitting the second energy waves along the length of the catheter at the second frequency in one or more pulses. In some embodiments, when the difference between the electrical signal and the baseline signal meets the threshold value, this may indicate occlusion of the catheter or one or more blood clots so large that if the blood clots became dislodged from the catheter, the blood clots could harm the patient.

In some embodiments, the baseline electrical signal may be determined by transmitting, via the transmitters 102, third ultrasonic waves along the length of the catheter when the catheter is open or unoccluded and converting a portion of the third ultrasonic waves that are reflected back from the catheter to the baseline electrical signal. In some embodiments, the baseline electrical signal may be determined prior to transmitting the first energy waves along the length of the intravenous catheter and/or converting the portion of the first energy waves that are reflected back from the intravenous catheter to the corresponding electrical signal. For example, the baseline electrical signal may be determined immediately after or shortly after insertion of the catheter into the vein of the patient. In some embodiments, the baseline electrical signal may be determined using another catheter similar or identical to the catheter. In some embodiments, the other ultrasonic waves may be equivalent to the ultrasonic waves. For example, the other ultrasonic waves and the ultrasonic waves may have the same frequency, amplitude, etc.

In some embodiments, the difference between the electrical signal and the baseline electrical signal may correspond to a difference in amplitude and/or frequency between the portion of the first energy waves that are reflected back from the catheter when the catheter is tested for occlusion and the portion of the third ultrasonic waves that are reflected back from the intravenous catheter when the catheter is unoccluded. In some embodiments, the difference between the electrical signal and the baseline electrical signal may be due to a state change within the catheter. For example, a larger difference between the electrical signal and the baseline signal may occur in response to presence of one or more blood clots within the catheter. In some embodiments, the larger the difference between the electrical signal and the baseline electrical signal, the more likely the catheter is occluded or likely to become occluded. In some embodiments, the threshold value may indicate a likelihood of one or more blood clots large enough to cause harm to the patient or a state of the blood within the catheter that may cause harm to the patient if vibration of the distal tip were to occur. In some embodiments, the threshold value may indicate occlusion of the catheter.

Figure 2A:
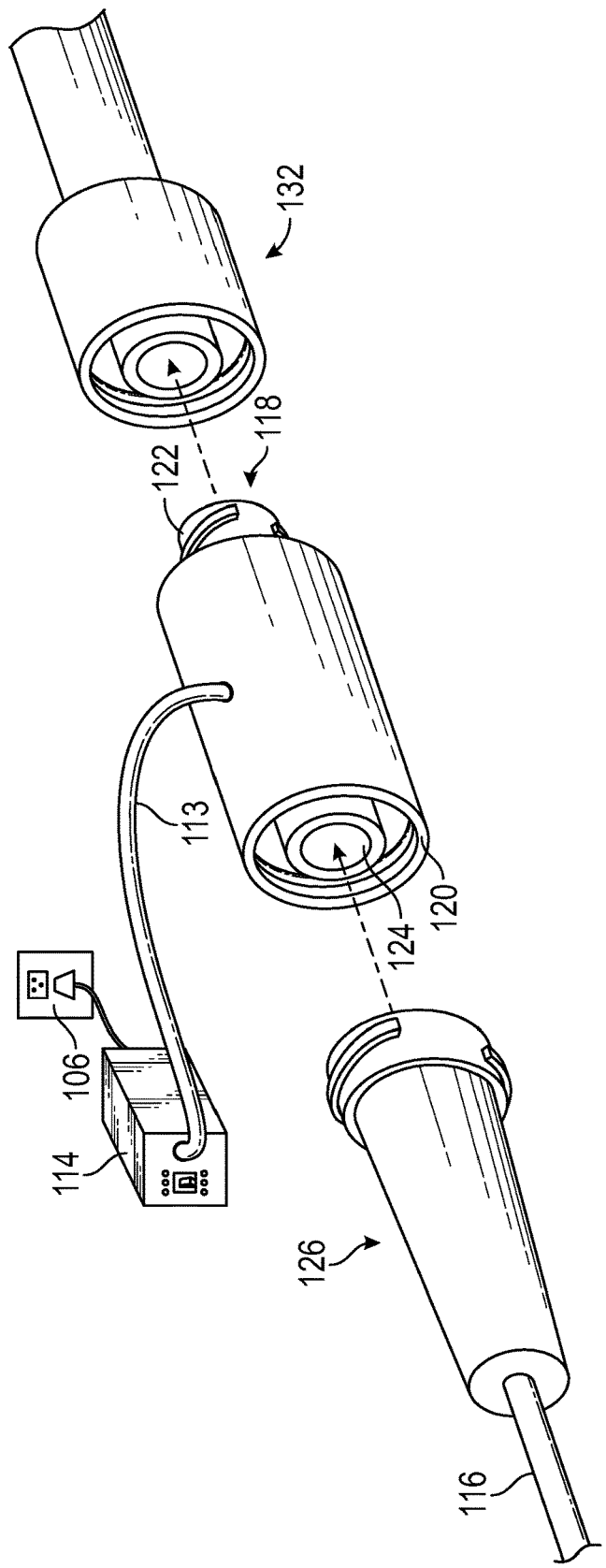
FIG. 2A illustrates an exploded view of the system, according to some embodiments.
Figure 2B:
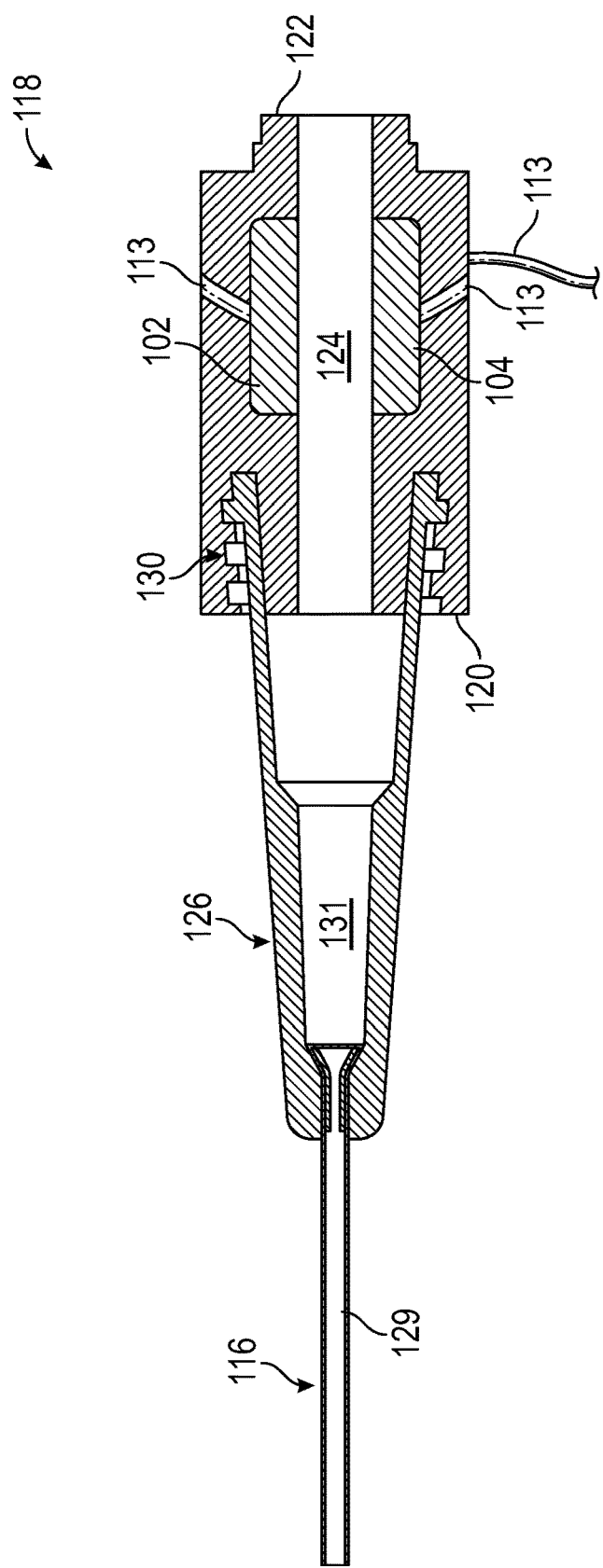
FIG. 2B illustrates a cross-sectional view of a portion of the system, according to some embodiments.

Referring now to FIGS. 2A-2B, in some embodiments, the system 100 to detect occlusion of the catheter 116 may include a housing 118, which may include a distal end 120, a proximal end 122, and an inner lumen 124 forming a fluid pathway. In some embodiments, the inner lumen 124 may extend between the distal end 120 and the proximal end 122 of the housing 118.

In some embodiments, the system 100 may include a catheter adapter 126. In some embodiments, the catheter 116 may extend distally from a distal end 128 of the catheter adapter 126. In some embodiments, the fluid pathway may extend through an inner lumen 129 of the catheter 116 and an inner lumen 131 of the catheter adapter 126, which may be continuous. In some embodiments, the distal end 120 of the housing 118 may be configured to couple to a proximal end 130 of the catheter adapter 126. In some embodiments, the proximal end 130 of the catheter adapter 126 and the distal end 120 of the housing 118 may be threadedly coupled together. In some embodiments, the proximal end 122 of the housing 118 may be configured to receive an IV line via a Luer device 132, which may be threadedly coupled to the proximal end 122.

In some embodiments, the transmitters 102 and/or the transducers 104 may be disposed in the fluid pathway, disposed partially within the fluid pathway, or separated from the fluid pathway by a buffer element, such as, for example, a membrane, coating, adhesive, or another suitable element. In some embodiments, the housing 118 may be coupled with the catheter adapter 126. In some embodiments, the housing 118 may be integrally formed with the catheter adapter 126 and/or may include or correspond to a portion of the catheter adapter 126. In some embodiments, the transmitters 102 and/or the transducers 104 may be embedded or encapsulated in a wall of the inner lumen of the housing 118.

In some embodiments, the transmitters 102 may transmit the first energy waves along an entire length of the catheter 116 of the catheter adapter 126 and/or throughout an entire lumen 129 of the catheter 116. Additionally or alternatively, in some embodiments, the transmitters 102 may transmit the second energy waves along the entire length of the catheter 116 of the catheter adapter 126 and/or throughout the entire lumen 129 of the catheter 116. In some embodiments, the signal generator 114 may be electrically coupled to the transmitters 102 via an electrical connector 113, which may extend through an opening in the housing 118. The entire length of the catheter 116 may extend from a proximal end to a distal end of the catheter 116. In some embodiments, the first and/or second energy waves may be transmitted along the length of the catheter 116 through the inner lumen 129 of the catheter 116 and/or may be aided by a wave guide disposed within the catheter 116 and/or catheter adapter 126. In some embodiments, the wave guide may include one or more conductive strips along a wall forming the inner lumen 129.

Referring now to FIG. 2D, in some embodiments, the transmitters 102 may be disposed in the wall of the housing 118, and the first and/or second energy waves may be transmitted from the transmitters 102 along the length of one or more of the following via one or more wave guides 135: the housing 118, the catheter adapter 126, and the catheter 116. In these and other embodiments, the first and/or second energy waves may include infrared, visible light, ultraviolet light, or other electromagnetic waves. As illustrated in FIG. 2D, in some embodiments, the wave guides 135 may extend from a particular transmitter 102 through the wall of the housing 118 to a distal end of the housing 118. In some embodiments, the first and/or second energy waves travelling along the wave guides 135 may emerge at the distal end of the housing and continue through the catheter adapter 126 and/or the catheter 116. In some embodiments, the wave guides 135 may include light guides or optical fibers.

Figure 2C:
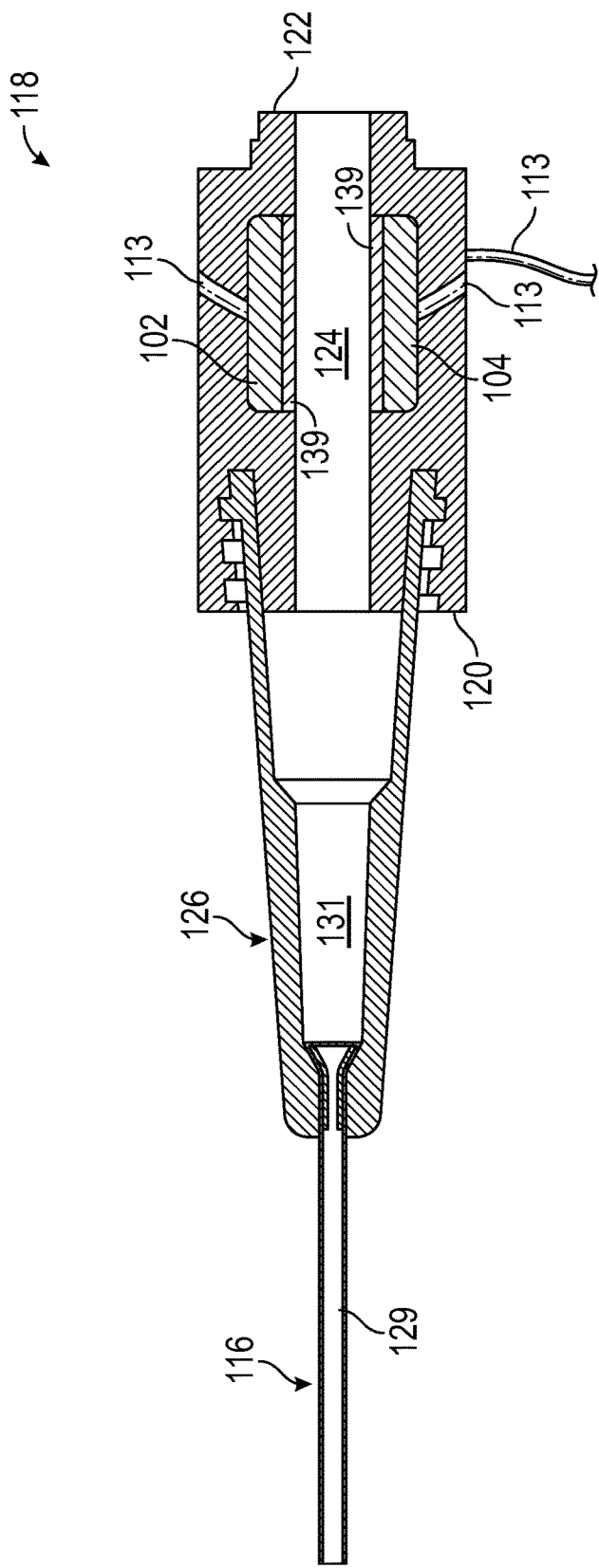
FIG. 2C illustrates another cross-sectional view of the portion of the system, according to some embodiments.

Referring now to FIG. 2E, in some embodiments, the transmitter 102 may be external to the housing 118 and/or the catheter adapter 126. In some embodiments, the first and/or second energy waves may be transmitted from the external transmitter 102 through the wall of the housing 118 via the one or more wave guides 135. In some embodiments, the wave guides 135 may extend through the wall of the housing 118 to the distal end of the housing. In some embodiments, the first and/or second energy waves travelling along the wave guides 135 may emerge at the distal end of the housing and continue through the catheter adapter 126 and/or the catheter 116. Referring to both FIGS. 2D and 2E, in some embodiments, the transducers 104 may be disposed as illustrated in FIGS. 2B or 2C or in any location within the housing 118 that allows the transducers 104 to detect the portion of the first energy waves that are reflected back from the catheter 116.

Figure 3A:
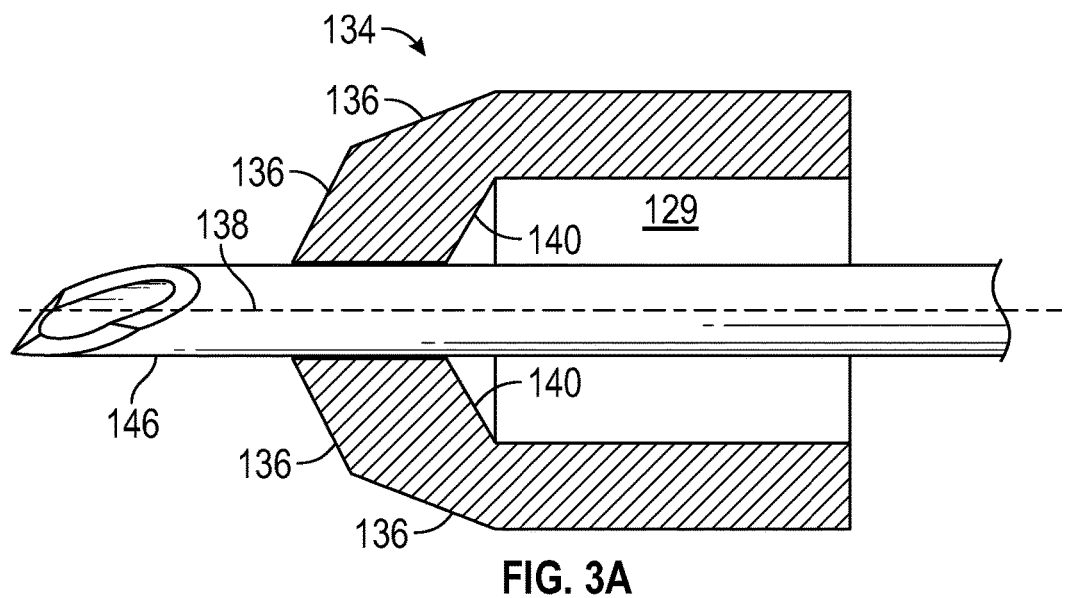
FIG. 3A illustrates a cross-sectional view of an example distal tip of an example catheter of the system, according to some embodiments.

Referring now to FIG. 3A, in some embodiments, an outer surface of a distal tip 134 of the catheter 116 may include one or more outer facets 136 or flat surfaces, which may be angled with respect to a longitudinal axis 138 of the catheter 116. In some embodiments, the facets 136 may improve reflection of the energy waves. Additionally or alternatively, in some embodiments, the wall forming the inner lumen 129 of the catheter 116 may include one or more inner facets 140, which may improve the reflection of the energy waves. In some embodiments, the inner facets 140 may be proximal to and proximate a portion of the tip 134 configured to contact an introducer needle 146 when the introducer needle 146 is inserted into a vein of the patient and prior to withdrawal of the introducer needle. In some embodiments, the outer surface and/or the inner surface of the distal tip 124 may be symmetric about the longitudinal axis 138.

Figure 3B:
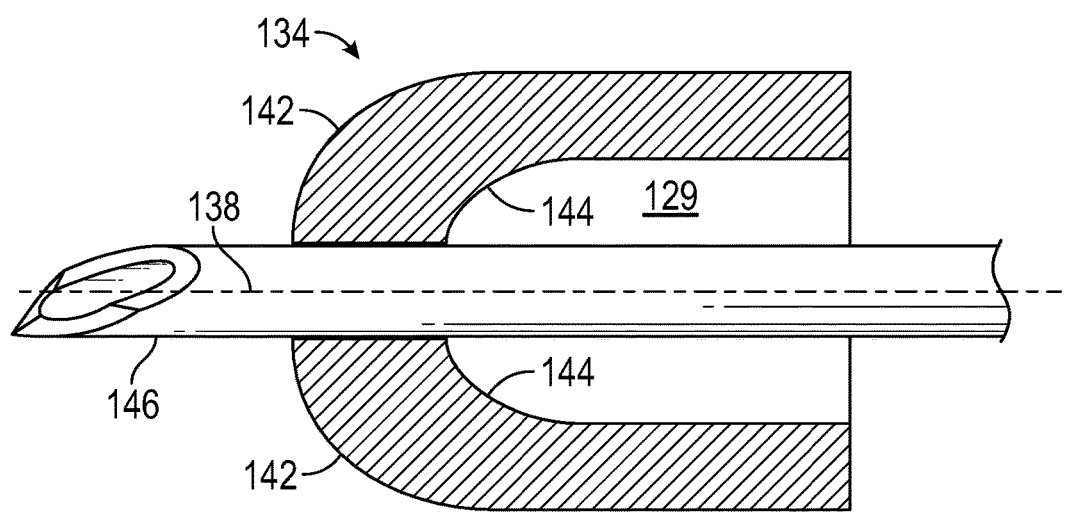
FIG. 3B illustrates a cross-sectional view of another example distal tip of an example catheter of the system, according to some embodiments.

Referring now to FIG. 3B, in some embodiments, an outer surface of the distal tip 134 of the catheter 116 may include one or more outer curved portions 142, which may improve reflection of the energy waves. Additionally or alternatively, in some embodiments, the wall forming the inner lumen 129 of the catheter 134 may include one or more inner curved portions 144, which may improve the reflection of the energy waves. In some embodiments, the inner curved portions 114 may extend from a portion of the tip 134 configured to contact an introducer needle 146 proximally to a proximal end of the catheter 116. The contact between the portion of the tip 134 and the introducer needle 146 may occur when the introducer needle 146 is inserted into a vein of the patient and prior to withdrawal of the introducer needle.

Figure 3C:
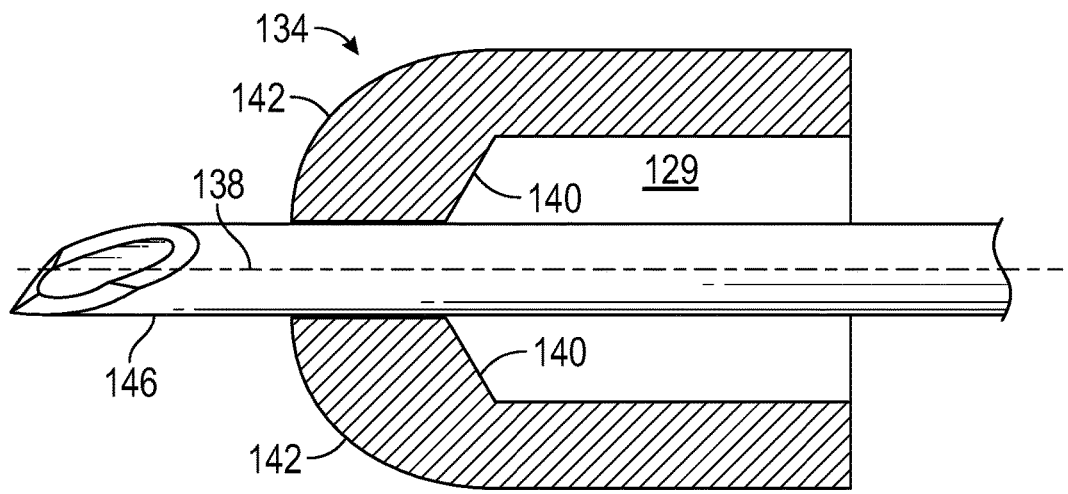
FIG. 3C illustrates a cross-sectional view of another example distal tip of an example catheter of the system, according to some embodiments.
Figure 3D:
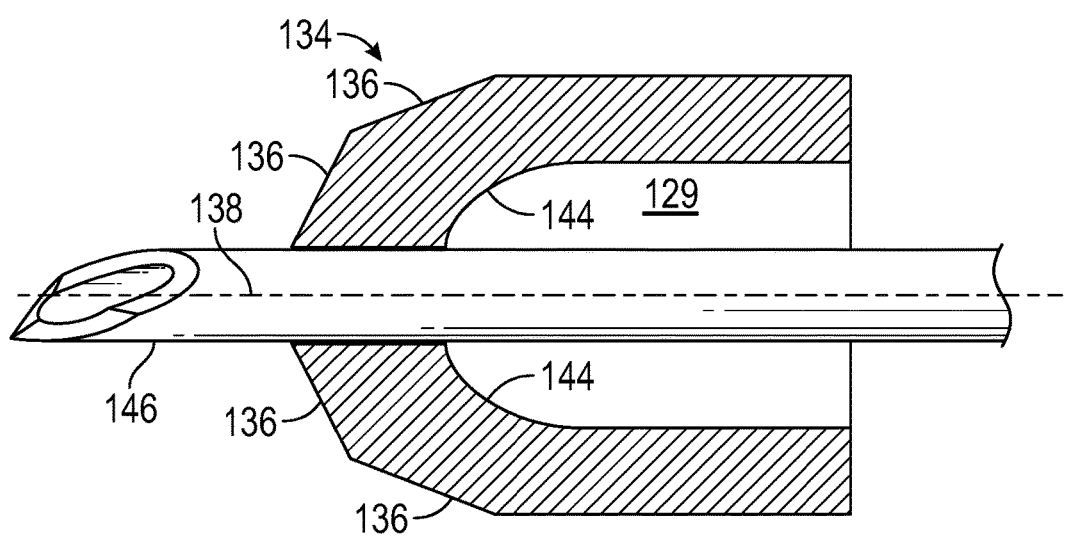
FIG. 3D illustrates a cross-sectional view of another example distal tip of an example catheter of the system, according to some embodiments.

Referring now to FIG. 3C, in some embodiments, the distal tip 134 may include the outer curved portions 142 and the inner facets 140, which may improve the reflection of the energy waves. Referring now to FIG. 3D, in some embodiments, the distal tip 134 may include the outer facets 136 and the inner curves 144, which may improve the reflection of the energy waves.

Figure 4:
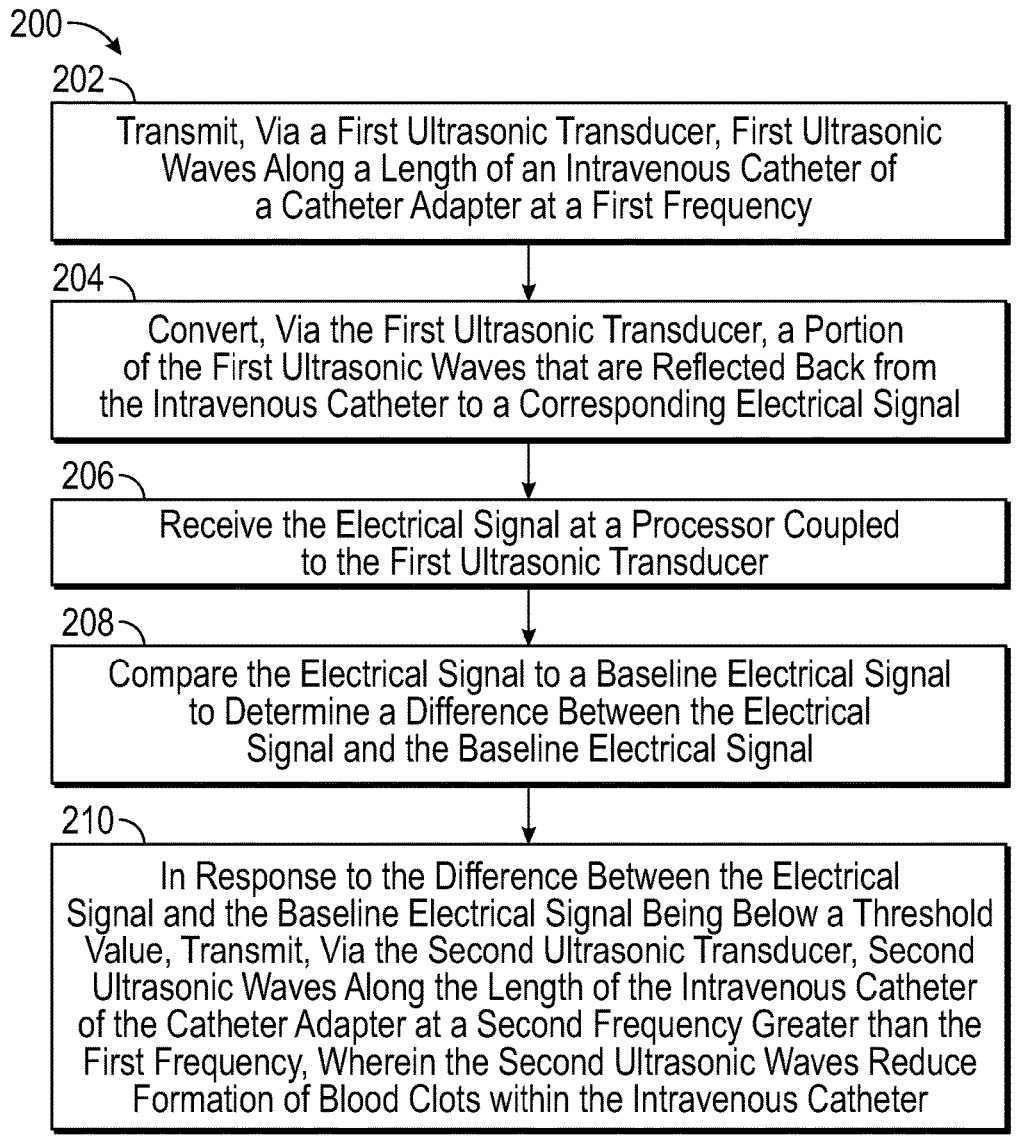
FIG. 4 illustrates a block diagram of an example method to prevent catheter occlusion using the system, according to some embodiments.

Referring now to FIG. 4, an example method 200 of preventing IV catheter occlusion may begin at block 202 in which first energy waves may be transmitted, via one or more transmitters, along a length of an IV catheter of a catheter adapter at the first frequency. In some embodiments, each of the transmitters may correspond to a particular transmitter 102 of FIGS. 1-2. In some embodiments, the catheter and catheter adapter may include or correspond to the catheter 116 and the catheter adapter 126 of FIGS. 2A-2B. Block 202 may be followed by block 204.

At block 204, a portion of the first energy waves that are reflected back from the intravenous catheter may be converted, via a transducer, to a corresponding electrical signal. Block 204 may be followed by block 206.

At block 206, the electrical signal may be received at a processor, which may be coupled to the transducer. The processor may include or correspond to the processor 108 of FIG. 1. Block 206 may be followed by block 208.

At block 208, the electrical signal may be compared to a baseline electrical signal to determine a difference between the electrical signal and the baseline electrical signal. Block 208 may be followed by block 210.

At block 210, in response to the difference between the electrical signal and the baseline electrical signal being below a threshold value, second energy waves may be transmitted, via the transmitters, along the length of the intravenous catheter of the catheter adapter at the second frequency, which may be greater than the first frequency. In some embodiments, the second energy waves may reduce formation of blood clots within the intravenous catheter. In some embodiments, the transducer may correspond to a particular transducer 104 of FIGS. 1-2.

Figure 5:
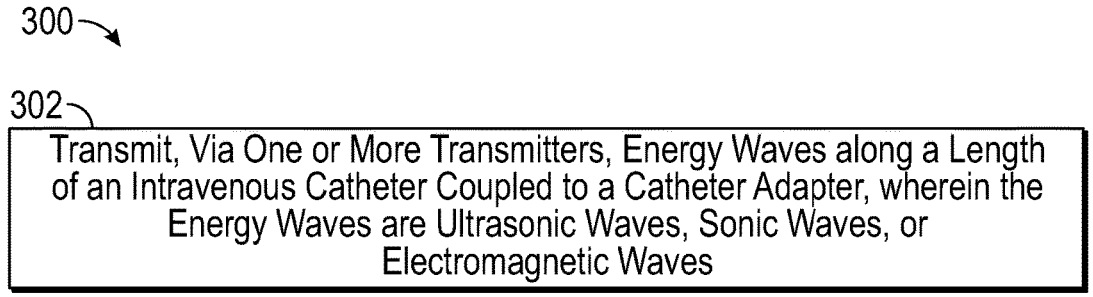
FIG. 5 illustrates a block diagram of another example method to prevent catheter occlusion using the system, according to some embodiments.

Referring now to FIG. 5, an example method 300 of preventing IV catheter occlusion may begin at block 302 in which energy waves are transmitted, via one or more transmitters, along a length of an intravenous catheter coupled to a catheter adapter. In some embodiments, the energy waves may include ultrasonic waves, sonic waves, or electromagnetic waves. In some embodiments, the one or more transmitters may transmit the energy waves along the length of the intravenous catheter at regular intervals or continuously.

Although illustrated as discrete blocks, various blocks may be divided into additional blocks, combined into fewer blocks, or eliminated, depending on the desired implementation. In some embodiments, the methods 200 and/or 300 may include additional blocks. For example, in some embodiments, the method 200 may include providing one or more of the following: a housing, the transmitters, the transducer, and the catheter adapter. In some embodiments, the housing may include or correspond to the housing 118 of FIGS. 2A-2B, and the transducer may include or correspond to the transducer 104 of FIG. 1. As another example, in some embodiments, the method 200 may include determining the baseline electrical signal, wherein determining the baseline electrical signal comprises transmitting other ultrasound waves along the length of the intravenous catheter when the intravenous catheter is unoccluded and converting a portion of the other ultrasound waves that are reflected back from the intravenous catheter to the baseline electrical signal.

The present invention may be embodied in other specific forms without departing from its structures, methods, or other essential characteristics as broadly described herein and claimed hereinafter. In some embodiments, the housing 118 of FIGS. 1-2 may not be directly coupled to the catheter adapter 126 and/or the luer device 132. For example, the system 100 of FIGS. 1-2 may include a needle safety mechanism, which may be disposed in between the catheter adapter 126 and the housing 118 or at another location. In these and other embodiments, the housing 118 may be integrally formed with the catheter adapter 126 and/or may include or correspond to a portion of the catheter adapter 126. Thus, in some embodiments, the transmitters 102 and/or the transducers 104 may be disposed within the catheter adapter 126, as opposed to a separate housing 118.

As a further example, the catheter adapter 126 may include various configurations. In some embodiments, the catheter adapter 126 may include a side port, a septum, a septum actuator, or one or more other elements. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A system to prevent occlusion of an intravenous catheter, comprising:
   a housing, comprising:
      one or more transmitters, wherein the one or more transmitters transmit first energy waves along a length of an intravenous catheter of a catheter adapter at a first frequency, wherein the one or more transmitters also transmit second energy waves along the length of the intravenous catheter of the catheter adapter at a second frequency, wherein the second frequency is greater than the first frequency; and
      one or more transducers configured to detect a portion of the first energy waves that are reflected back from the intravenous catheter; and
   a processor coupled to the transmitter, wherein the processor receives an electrical signal corresponding to the portion of the first energy waves that are reflected back from the intravenous catheter and compares the electrical signal to a baseline electrical signal to determine a difference between the electrical signal and the baseline electrical signal, wherein the one or more transmitters transmit the second energy waves along the length of the intravenous catheter at the second frequency in response to the difference between the electrical signal and the baseline electrical signal being below a threshold value, wherein the one or more transmitters are prevented from transmitting the second energy waves along the length of the intravenous catheter at the second frequency in response to the difference between the electrical signal and the baseline electrical signal meeting the threshold value.

2. The system of claim 1, wherein the one or more transducers comprise a first transducer and a second transducer, wherein the first transducer comprises a first piezoelectric crystal, wherein the second transducer comprises a second piezoelectric crystal, wherein the first and second piezoelectric crystals are embedded or encapsulated in a wall of the inner lumen.

3. The system of claim 1, wherein an outer surface of a distal tip of the intravenous catheter comprises a plurality of facets.

4. The method of claim 1, wherein a wall forming an inner lumen of the intravenous catheter comprises one or more inner curved portions that extend proximally from a portion of a distal tip of the intravenous catheter configured to contact an introducer needle.

5. The system of claim 1, wherein the one or more transmitters transmit the second energy waves along the length of the intravenous catheter of the catheter adapter at the second frequency in pulses.

6. The system of claim 1, wherein the second frequency is between 300 and 700 kHz.

7. The system of claim 1, wherein the first frequency is less than or equal to 300 kHz.

8. A system to prevent occlusion of an intravenous catheter, comprising:
   a housing, comprising:
      one or more transmitters, wherein the one or more transmitters transmit first energy waves along a length of an intravenous catheter of a catheter adapter at a first frequency, wherein the one or more transmitters also transmit second energy waves along the length of the intravenous catheter of the catheter adapter at a second frequency, wherein the second frequency is greater than the first frequency, wherein a wall forming an inner lumen of the intravenous catheter comprises one or more inner curved portions that extend proximally from a portion of a distal tip of the intravenous catheter configured to contact an introducer needle; and
      one or more transducers configured to detect a portion of the first energy waves that are reflected back from the intravenous catheter; and
   a processor coupled to the transmitter, wherein the processor receives an electrical signal corresponding to the portion of the first energy waves that are reflected back from the intravenous catheter and compares the electrical signal to a baseline electrical signal to determine a difference between the electrical signal and the baseline electrical signal.

9. The system of claim 8, wherein the one or more transmitters transmit the second energy waves along the length of the intravenous catheter at the second frequency in response to the difference between the electrical signal and the baseline electrical signal being below a threshold value.

10. The system of claim 9, wherein the one or more transmitters are prevented from transmitting the second energy waves along the length of the intravenous catheter at the second frequency in response to the difference between the electrical signal and the baseline electrical signal meeting a threshold value.

11. The system of claim 8, wherein the one or more transducers comprise a first transducer and a second transducer, wherein the first transducer comprises a first piezoelectric crystal, wherein the second transducer comprises a second piezoelectric crystal, wherein the first and second piezoelectric crystals are embedded or encapsulated in a wall of the inner lumen.

12. The system of claim 8, wherein an outer surface of a distal tip of the intravenous catheter comprises a plurality of facets.

13. The method of claim 8, wherein a wall forming an inner lumen of the intravenous catheter comprises one or more inner curved portions that extend proximally from a portion of a distal tip of the intravenous catheter configured to contact an introducer needle.

14. The system of claim 8, wherein the one or more transmitters transmit the second energy waves along the length of the intravenous catheter of the catheter adapter at the second frequency in pulses.

15. The system of claim 8, wherein the second frequency is between 300 and 700 kHz.

16. The system of claim 8, wherein the first frequency is less than or equal to 300 kHz.

* * * * *